(12) United States Patent
Strauss et al.

(10) Patent No.: US 6,189,327 B1
(45) Date of Patent: Feb. 20, 2001

(54) EVAPORATIVE PERSONAL COOLER

(76) Inventors: Ted N. Strauss, 145 Canvon Rd., Fairfax, CA (US) 94930; Charles E. Taylor, 446 West St., Sebastopol, CA (US) 95472

( * ) Notice: Under 35 U.S.C. 154(b), the term of this patent shall be extended for 0 days.

(21) Appl. No.: 09/148,843

(22) Filed: Sep. 4, 1998

Related U.S. Application Data

(63) Continuation-in-part of application No. 08/924,580, filed on Sep. 5, 1997, now Pat. No. 5,802,865.

(51) Int. Cl.[7] .............................. F25D 5/00; F25D 23/12
(52) U.S. Cl. ............................................. 62/259.3; 62/314
(58) Field of Search ................................. 62/259.3, 314, 62/304, 121; 2/458, DIG. 1, DIG. 11

(56) References Cited

U.S. PATENT DOCUMENTS

| | | |
|---|---|---|
| 1,633,586 | 6/1927 | Hunter . |
| 1,907,709 | 5/1933 | Barrow . |
| 2,160,567 | 5/1939 | Sterne ...................................... 2/171 |
| 2,223,332 | 11/1940 | Sterne ...................................... 2/171 |
| 2,783,474 | 3/1957 | Campagna et al. ...................... 2/171 |
| 2,832,077 | 4/1958 | McGinnis ................................. 2/171 |
| 3,029,438 | 4/1962 | Henschel ...................................... 2/7 |
| 3,096,702 * | 7/1963 | Malone et al. ....................... 62/259.3 |
| 3,296,819 | 1/1967 | Gough ..................................... 62/259 |
| 3,429,138 * | 2/1969 | Goldmerstein ....................... 62/259.3 |
| 3,466,664 | 9/1969 | Militello .................................. 2/171 |
| 3,610,323 | 10/1971 | Troyer ..................................... 165/46 |
| 4,130,902 | 12/1978 | Mackenroth, III et al. ................. 2/7 |
| 4,742,581 | 5/1988 | Rosenthal ................................. 2/181 |
| 4,893,356 | 1/1990 | Waters ................................. 2/171.3 |
| 5,146,765 | 9/1992 | Waters ............................... 62/259.3 |
| 5,175,887 | 1/1993 | Kim ........................................ 2/174 |
| 5,564,124 | 10/1996 | Elsherif et al. ............................ 2/69 |
| 5,802,865 * | 9/1998 | Strauss ............................... 62/259.3 |

* cited by examiner

*Primary Examiner*—William Doerrler
(74) *Attorney, Agent, or Firm*—Flehr Hohbach Test Albritton & Herbert LLP

(57) ABSTRACT

A self-contained evaporative personal cooling device fits conformally around a user's neck or other body portion. The device includes at least one heat dissipating member that is urged conformably against the body portion to absorb heat therefrom. The device-facing side of this member preferably has a large surface area with a liquid-wickable surface. A liquid-retainable material contacts at least a portion of the wickable surface area and also defines at least one air plenum. Ambient air is moved along the plenum, preferably by a battery-powered fan. The air transfers heat from the member, cooling the user, and is exhausted from the device. A thermostat can sense temperature at the heat dissipating member to control duty cycle of the fan to prevent overcooling the user.

20 Claims, 8 Drawing Sheets

EVAPORATIVE PERSONAL COOLER

RELATIONSHIP TO OTHER APPLICATION

This is a continuation-in-part of application Ser. No. 08/924,580 filed Sep. 5, 1997, now U.S. Pat. No. 5,802,865 issued Sep. 8, 1998.

FIELD OF THE INVENTION

The present invention relates generally to personal cooling devices, and more particularly to evaporative coolers that are worn around the neck or head of a user.

BACKGROUND OF THE INVENTION

Individuals often wish to be cooled, especially in warm ambient temperatures. The desire to be cooled may arise indoors or out, while exercising, engaging in sports, driving, or being in an environment that is not comfortably cool.

It is known in the art to provide a cap to be worn by an individual that can provide some cooling. U.S. Pat. No. 5,365,607 to Benevento, for example, discloses a cap whose headband includes a plurality of tapered porous pads. The pads are wet with water and apparently produce a cooling effect to the user's head as the water evaporates.

U.S. Pat. No. 3,029,438 to Henschel discloses a water-cooled cap in which an inner aluminum strip contacts the wearer's head, and is contacted with a water absorbent sponge strip (or strips), in turn over-covered by a fabric. The sponge material is wet, and as the water evaporates, the aluminum strip cools, thus cooling the wear's head.

U.S. Pat. No. 4,130,902 to Mackenroth discloses a cooling hat band that includes an outer support band, an inner absorbent band, a wicking element and a water reservoir. Reservoir water moves along the wicking element to the absorbent band, whence it evaporates, passing through holes in the support band. The evaporative effect is said to remove heat from the headband, and thus from the wear's forehead.

However, not all individuals like to wear caps, and participation in some sports, e.g. bicycling, may dictate that another type of headgear be worn, a helmet for example. Thus, several attempts have been made in the prior art to improve upon a basic cooling band, such as a tennis player might wear around the forehead. For example, U.S. Pat. No. 4,742,581 to Rosenthal discloses a laminated cooling band comprising a skin-contacting air pervious heat conductive layer edge-connected to an air pervious fabric that is moistened with water exposed to ambient air. This device is said to cool the wearer as water evaporates from the outer fabric. However, as is typical with many prior art devices, evaporative cooling is dependent upon ambient air motion. If the wearer is stationary, the efficiency of evaporative cooling decreases.

Notwithstanding the above devices, there is a need for a self-contained personal evaporative cooling device that promotes efficient cooling. If worn about the user's neck, such device should not require headgear. Further, such device should be useable on other portions of the user's body, the forehead, for example. Preferably such device should enhance evaporative cooling by maximizing the heat sinking area, maintaining a thin film of liquid upon such area, and by circulating air within the device. Such device should be simple to use and wear, and should provide cooling that lasts for several hours without replenishment of liquid or energizing source. The present invention provides such a cooling device.

SUMMARY OF THE PRESENT INVENTION

A preferred embodiment of the present invention is a self-contained evaporative personal cooling device in the form of a C-shaped band that fits conformally around a portion of a user's body, e.g., the neck or forehead. The device includes an articulated housing within which is disposed a heat sinking or dissipating member, preferably implemented as a plurality of side-edge-joined metal plates that each have a first, neck-facing surface, and a second, opposite, surface. The metal plates are urged conformably against the user's neck or forehead such that the first, or exterior plate, surfaces contact the neck. A water-retaining preferably foam-like sponge material is disposed within the housing in contact with the upper and/or lower surfaces or regions of the metal plates but spaced-apart from the second surface of the plate body to form a plenum therebetween. The sponge material is saturated with a liquid, preferably water, introduced through liquid intake slots in the housing, before the cooling device is to be used. The device includes a DC powered fan that draws air into the housing though air intake vents and then circulates the air within the plenum defined between the metal plates and the sponge material and out through air exit vent openings in the housing. Moisture from the sponge material wets the plenum-facing surface of the metal plates, and the fan-circulated air produces evaporation. The evaporation cools the metal plates, which absorb heat from the user's neck or forehead and thus cools the user.

Preferably the plenum-facing surfaces of the metal plates define pins, ridges, fins, or the like to increase plate surface area. To help promote the cooling process, a wicking material is used to coat at least portions of the ridged contact surface area. During device manufacture a surfactant is applied to the sponge material and to the preferably wicked surface areas of the metal plates to encourage capillary-like liquid migration and promote cooling efficiency. In use, a wicking action encourages water migration from the sponge material to the ridge surfaces of the metal plates. Preferably the plenum-facing surface of the sponge material is covered with a moisture barrier. However the moisture barrier does not cover regions where the sponge material contacts the metal plates or where the sponge material is adjacent housing slits through which water is introduced. The barrier helps maximize evaporation at the metal plates by preventing circulation of dry plenum air from evaporating water from the foam. Further, the barrier reduces water loss and water leakage. If desired, a color-changing material may be included to serve as a low water indicator. To promote efficiency, the fan blade preferably includes a centermost axial portion that draws air into the housing through input vents, and an outermost radial portion that circulates the air in the plenum within the housing. Alternatively the fan might be replaced with other air-moving means including electro-kinetic mechanisms that move air silently and without moving parts.

An alternative preferred embodiment provides a reverse air flow such that ambient air is drawn into the device at one or more generally forward or peripherally facing regions of the device, and warmed air is exhausted at a generally rear facing region of the device and/or along peripheral edges of the device. The ambient air may be drawn-in and exhausted actively by a motor, or may be drawn-in and exhausted passively, by relative forward motion of the device in the ambient air, e.g., when worn by a jogger, a bicyclist, etc.

In these and/or other embodiments, the preferably foam-like sponge liquid-retaining material need only contact the heat dissipating member at one location, for example in a central portion of the device-facing surface of the dissipating member. Indeed, the device-facing surface of the heat dissipating member may itself be a porous metal-type material, affixed or integral with the body portion-facing surface of the dissipating member, such the foam-like material can be eliminated. In such embodiment, one or more microplenums may be defined within the porous region of the dissipating member. In yet another embodiment, the heat dissipating member is made from a fabric such as felt cloth.

If desired, one or more pumps may be provided to spray a mist of water onto the device-facing surface of the heat dissipating member, and/or into fan-moved air in the plenum(s).

Other features and advantages of the invention will appear from the following description in which the preferred embodiments have been set forth in detail, in conjunction with the accompanying drawings.

DETAILED DESCRIPTION OF THE PREFERRED EMBODIMENT

Figure 1:
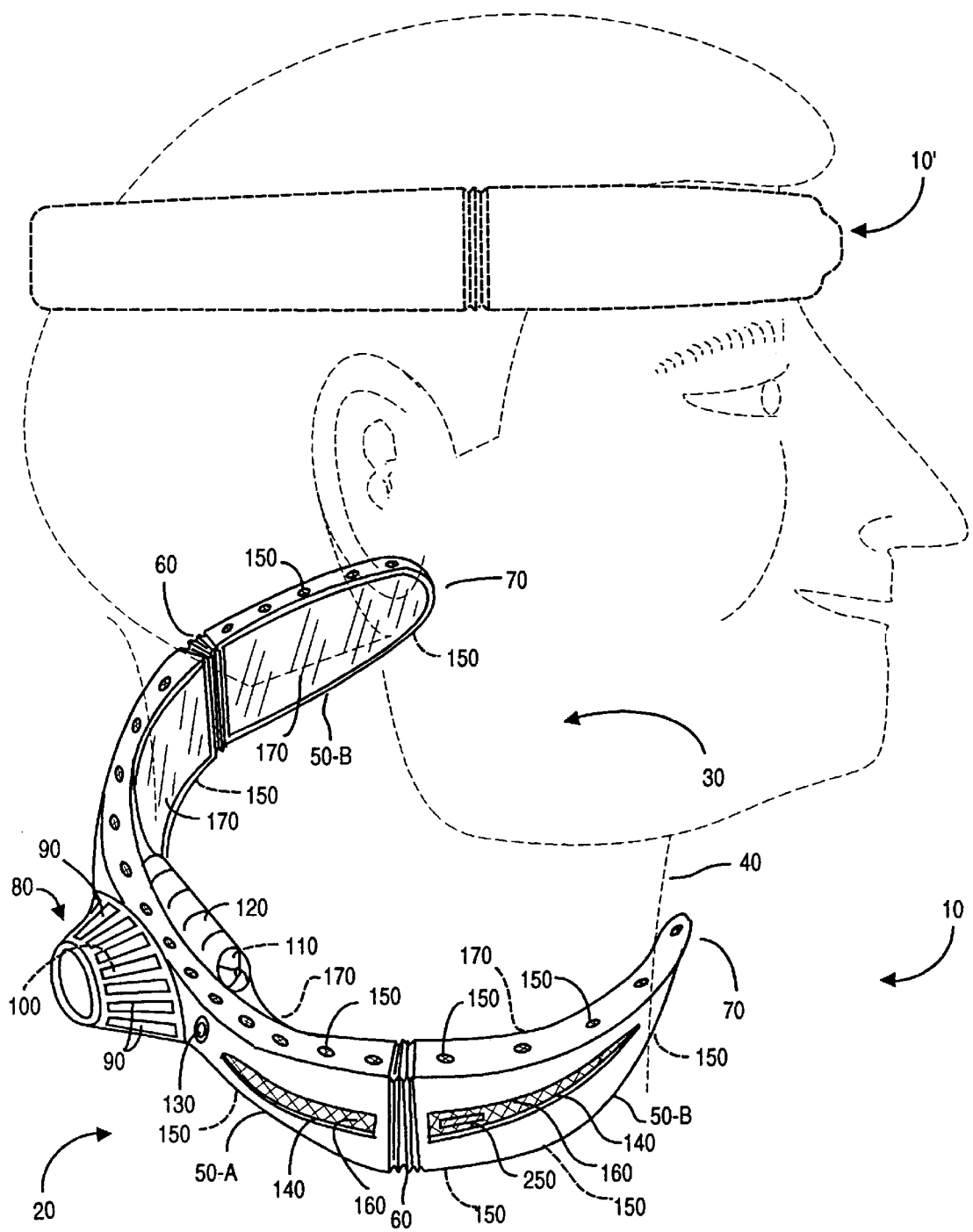
FIG. 1 is a perspective view of the present invention worn around the neck of a user.

FIG. 1 depicts an evaporative neck cooler 10 worn around the neck of a user, the user shown drawn in phantom lines. Alternatively, a cooler 10' may be worn in headband fashion around the forehead of a user, as shown in phantom. Hereinafter neck cooler 10 will be described, however it is to be understood that the description is also applicable to a forehead cooler 10'.

Cooler 10 includes a generally "C"-shaped housing 20 that preferably encircles at least 180° and includes an opening 30 sized to permit housing 20 to pass around the neck 40 of a user. In the preferred embodiment, housing 20 is formed of a plastic material and comprises a central housing portion 50-A and end portions 50-B, the portions being joined together by flexible linkages 60, that may be accordion or bellows-like in function. Collectively, portions 50-A and 50-B are biased by linkages 60, and/or by the material comprising housing 20 to urge cooler 10 to fit snugly but comfortably around the user's neck. Of course housing 20 should be sufficiently flexible and/or articulatable to permit easy removal of device 10 from a user's neck. Those skilled in the art will appreciate that more or fewer than two linkages 60 could be employed, and that if a suitably elastic housing material were used, possibly no linkages would be required. Preferably distal ends 70 of housing portions 50-B are rounded to promote user comfort in wearing cooler 10. (Obviously, a forehead cooler 10' will be sized to fit comfortably about the forehead of a user.)

Figure 2:
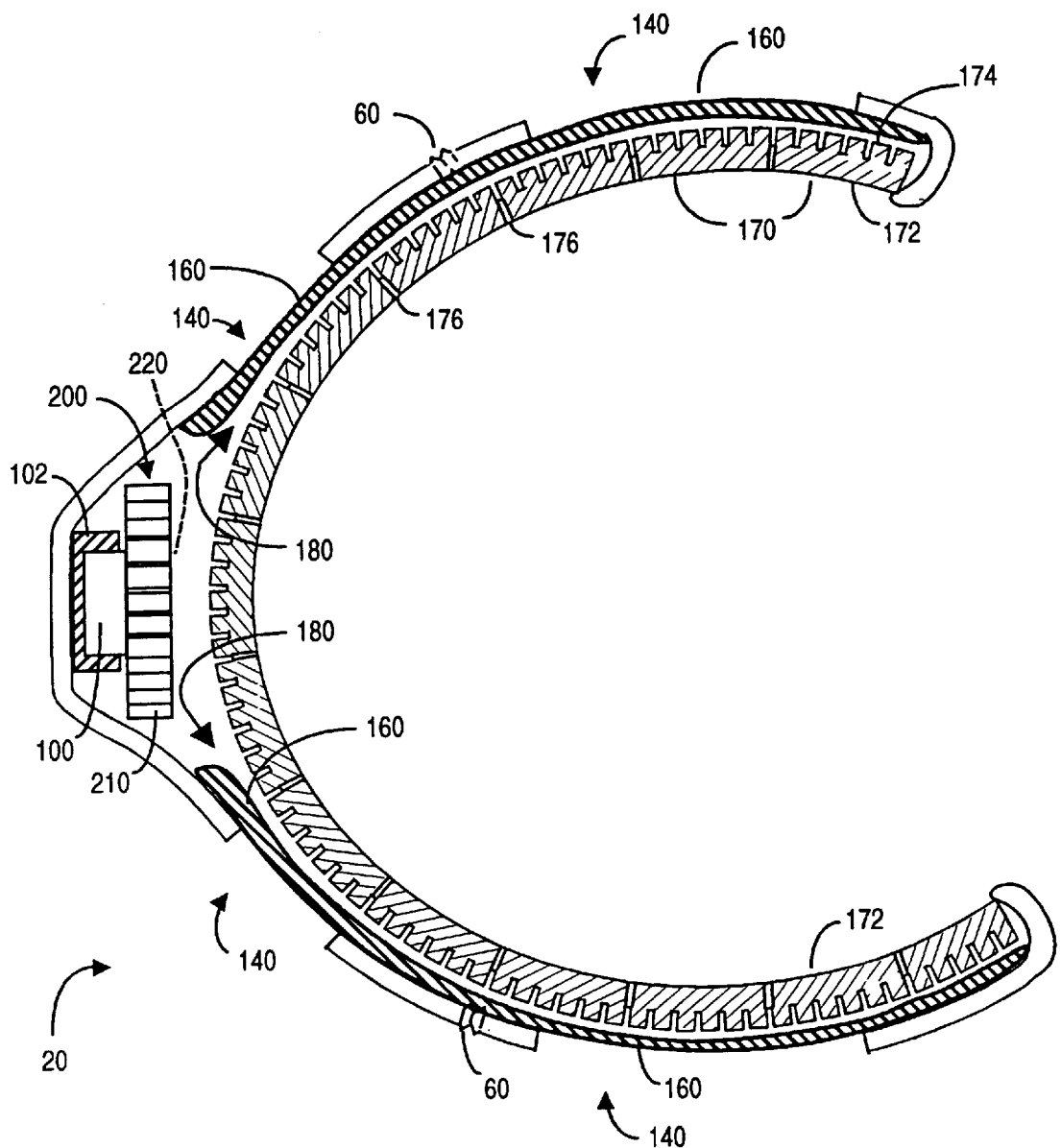
FIG. 2 is a cross-sectional view along the center of the present invention.

Preferably central housing portion 50-A includes a motor housing 80 having air intake vents 90, and a small DC motor 100 retained within a retainer cup 102 within housing 80. A battery 110 (e.g., a 1.5 VDC AA unit) is retained within a battery compartment 120 that may be formed on an adjacent region of housing 20. A user-accessible ON/OFF switch 130 enables the user to activate motor 100 by switcheably connecting/disconnecting battery 110 from the motor. (As shown in FIG. 2, when activated, motor 100 rotates a fan blade assembly 200.) Of course DC motor 100 may be powered by other than a battery. For example, solar cells might be disposed on the exterior surface of device 10 to generate motor operating potential. Alternatively, motor 100 might be a mechanical, wind-up type motor that requires no electrical operating potential.

Referring again to FIG. 1, preferably housing portions 50-A, 50-B include liquid intake or input slot openings 140 in their exterior surface, e.g., the housing surface that does not face toward the user's neck. Of course more or fewer slots can be provided than the number shown, and the shape of some or all of the slots may differ from what is depicted in FIG. 1. Preferably the upper and lower surfaces of the housing portions also include a plurality of air exit vent openings 150, to promote cooling. It is understood that the shape, number and location of vent openings 150 may differ from what is shown in FIG. 1. For example, substantially more such openings may be provided.

As best seen in FIGS. 1 and 2, cooler 10 further includes water (or liquid) retaining or absorbing material, preferably foam-like porous sponge material 160, that is disposed within housing 20 adjacent the inner wall of the housing exterior surface. When device 10 is used material 160 is saturated with liquid, preferably water, introduced via slots 140. Preferably material 160 is ordinary cellulose sponge, a material that can absorb water to saturation, and then retain the water without undue expulsion, e.g., by leaking out of housing 20 onto the user. Of course other materials with similar water retaining characteristics may be used for material 160. Experiments by applicant with open cell high density polyethylene foam including HDPE and PVA sponge indicate that while such material adequately retains water, water migration through the material is slower than if cellulose sponge material were used. However, material 160 need not necessarily be foam-like or spongy, and could instead be a fabric, or a non-woven material.

Cooler 10 also includes a heat dissipating member 170 that preferably is metal. Heat dissipating member 170 is retained by holder 20 such that the first dissipator surface 172 is urged against the neck of the user (see FIG. 2). Surface 172 draws body heat from the user's neck into the dissipator member 170. In the embodiment of FIG. 1, there is a single heat dissipating member 170 for each housing portion. However, a plurality of smaller heat dissipating members 170 may be provided in each housing portion as shown in FIG. 2, especially if the housing portions are sufficiently flexible.

As will be described, water-saturated sponge material 160 within housing 20 wets plenum-facing second surface 174 of member 170. An evaporation is promoted that lowers the temperature of surface 172, thus cooling the user's neck.

Figure 3:
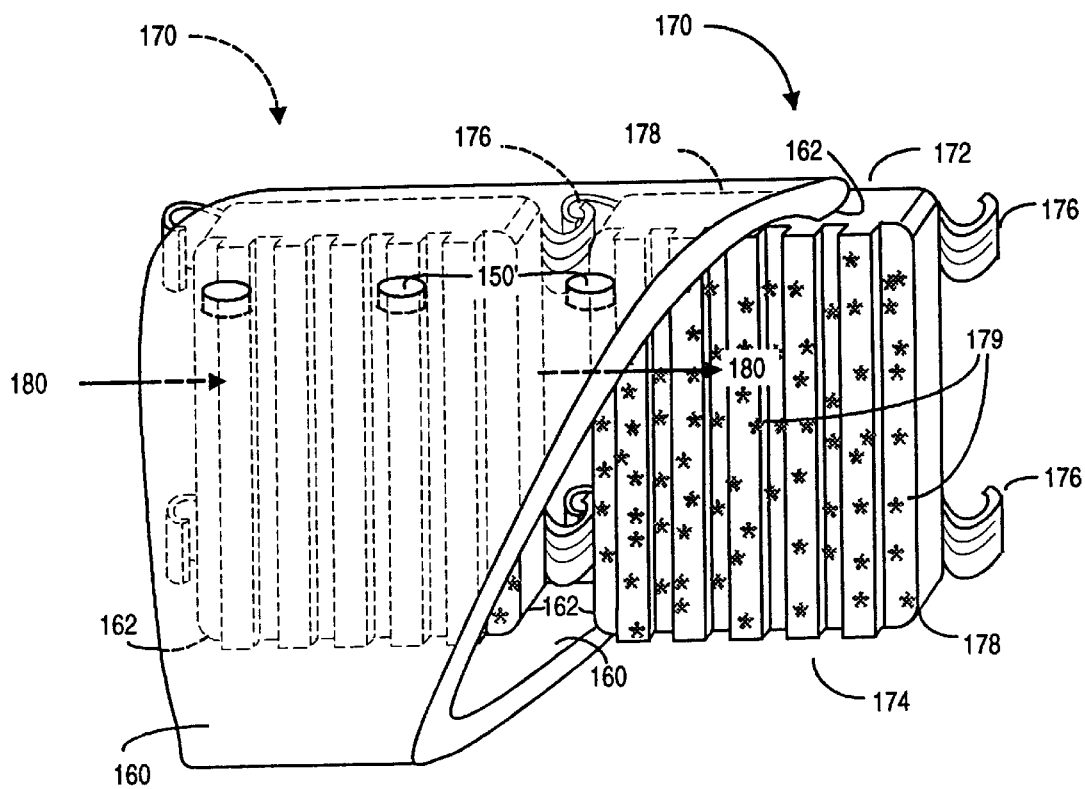
FIG. 3 is a perspective partial cutaway view depicting the plenum-facing side of the dissipator plates and sponge material and the resultant plenum, according to the present invention.

In the embodiments of FIGS. 2 and 3, the dissipating member comprises a plurality of aluminum plates or elements 170, joined vertical edge-to-vertical edge by mechanisms 176. Mechanisms 176 preferably are biased hinges that urge plates 170 to flexibly conform to the surface of the user's neck. Although mechanisms 176 are depicted in FIG. 3 as being hinge-like, other mechanisms that retain adjacent plates 170 while urging the plates to generally conform to the shape of a user's neck may be used instead. For example, mechanisms 176 could include hinges (including plastic flexible tape as hinges) that include a torsion spring to create a bias force. Mechanisms 176 might include a band of metal that creates a bias force, using either a separate band between adjacent plates 170, or one band to connect and bias many or indeed all of the plates 170.

Thus, it will be appreciated that heat dissipator member 170 might itself comprise a continuous band of flexible conductive material, or a separate such band for each housing portion (e.g., as shown in FIG. 1), rather than the plurality of plates depicted in FIG. 2. In such an implementation, there might be no need for separate bias or joining mechanisms 176. Regardless of the implementation, material 170 should be a good dissipator of heat, preferably be lightweight, and should be biased to conform generally and flexibly to the user's neck.

As best seen in FIGS. 2 and 3, portions of sponge material 160 preferably contact the upper and/or lower regions 178 of dissipator plates 170. However, exterior plate surface 174 is spaced-apart from material 160 such that plenums 180 are defined within housing 20. As will be described, fan 100 and fan blade assembly 200 move ambient air into housing 20 and along plenums 180 to promote evaporative cooling of the user's neck. FIG. 2 is intended to show the relative relationship of the components comprising device 10, and is not drawn strictly to scale. In practice plenums 180 may be larger than what is shown to promote more efficient cooling.

As noted, sponge material 160 is preferably saturated with water. To minimize loss of water through evaporation (other than at region(s) 178 of the dissipator plates), the outer surface or skin of material 160 preferably is coated or covered with a thin moisture barrier, a plastic film, for example. However, as shown in FIG. 3, at the interface 162 of the sponge material and dissipator plates regions 162 the barrier is not formed, (or if formed is removed) to promote water cooling of dissipator plates 170. Preferably such moisture barrier on material 160 is not formed (or removed if formed) adjacent slits 140 in housing 20, to facilitate loading the sponge material with water. The moisture barrier not only prevents air circulating in plenums 180 from evaporating water from the sponge material, but also reduces leakage of water onto the user's neck or clothing. Moisture loss may also be reduced by providing slots 140 with covers that are removed or hinged out of the way when adding water to cooler 10, but are otherwise closed. Note the presence of openings 150', which coincide in location with openings 150 in the upper and lower housing surfaces. Openings 150' may be larger than openings 150 but should not be smaller, to avoid impeding the air flow exiting the device housing.

The preferably somewhat flexible nature of housing 20 and material 60 is such that the dissipator plates 170 are urged towards the user's neck to make reasonably good thermal contact therewith. Heat from the user's neck is transferred at least in part to surface 172 of plates 170, which plates are cooled by the presence of water within sponge material 160.

To promote water-cooling of plates 170, a water wicking action is encouraged along plenum-facing surface 174 of dissipator plates 170. As seen in FIGS. 2 and 3, surface 174 preferably includes fins, projecting pins or rectangles or squares, or the like to increase surface area. It is understood that the configuration shown in FIGS. 2 and 3 is only exemplary, and that the drawings are not precisely scaled. In practice, a surface 174 having projecting pins rather than fins appears to promote more efficient heat transfer and cooling. In such an embodiment, heat transfer efficiency is promoted by forming dissipator plates 170 with many relatively thin, preferably pin-shaped, projections on plenum-facing side 174.

To promote migration of water from the sponge material into surface 174, a wicking material 179 is provided. Wicking material 179 preferably comprises silicon carbide powder, about 100 mesh, although 80 mesh aluminum powder may be used, among other wicking materials. A thin layer of glue is applied at least to regions of surface 174 of plates 170, and the wicking powder is dusted onto the glued regions. Applicant used commercially available Gorilla brand premium glue although other adhesives could be used. The plate with glued powder is then dried, e.g., for about 30 minutes at about 300° F. Alternatively, the heat dissipator plates could be flocked with a short fiber material, although applicant has experienced some inconsistency in temperature drops using various flocked coatings. As yet another alternative, surface 174 might be acid-etched or sandblasted to define a wicking surface, without using mesh powders and adhesives, or flocking material.

To further promote wicking and resultant cooling efficiency, a surfactant, e.g., household liquid dishwashing detergent, is applied to the wicking-coated surfaces of plates 170 during device manufacture. Preferably, sponge material 160 is soaked with the same surfactant during manufacture as well. It is anticipated that users will on occasion re-apply surfactant to the metal plates and sponge material, when cooling efficiency appears to have degraded.

Figure 4:
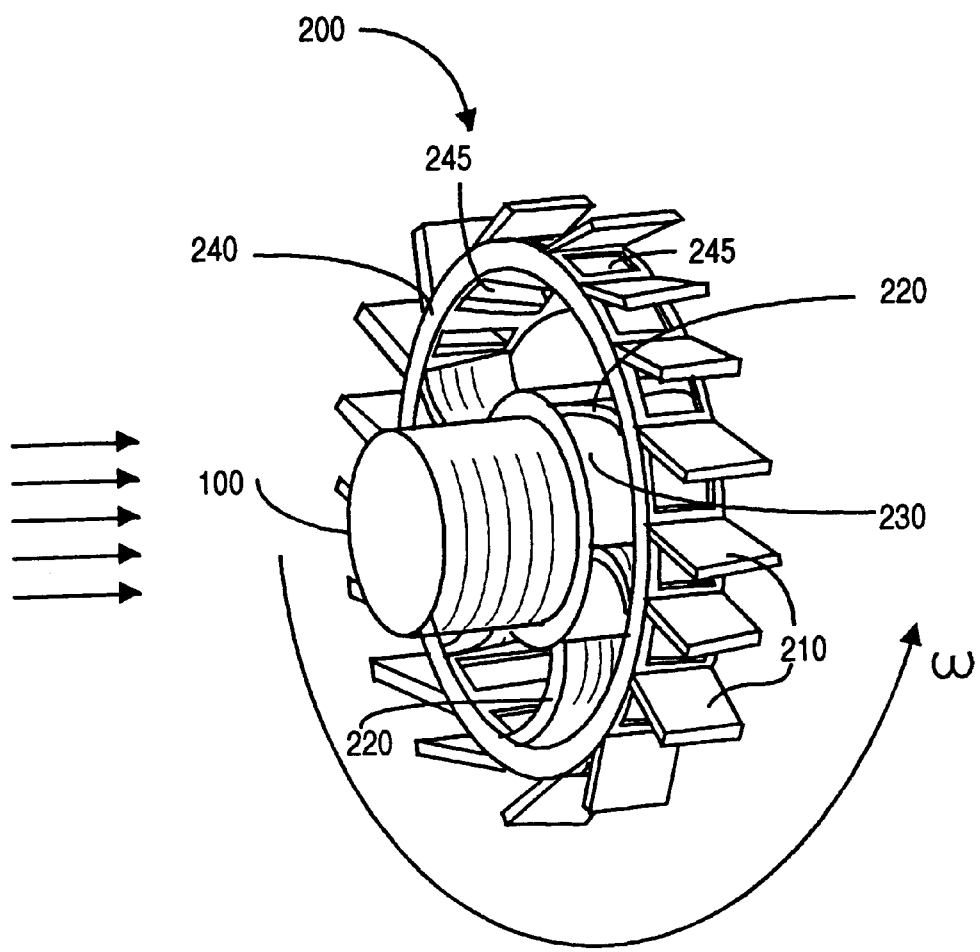
FIG. 4 is a perspective view of a motor and a preferred fan blade assembly, according to the present invention.

In using device 10, material 160 is saturated with water via openings 140. The evaporative neck cooler is then put around the user's neck (or forehead) and switch 130 turned ON. As battery 110 energizes motor 100, fan blade 200 rotates. As seen in FIG. 4, fan blade 200 preferably includes a radially configured outer blade portion 210, and an inner axially configured blade portion 220. Inner blade portion 220 is formed on a hub 230, and a second hub 240 is common to blade portions 210 and 220. Alternatively, fan blade 200 may comprise only axially disposed blades, or only radially disposed blades set at an angle that forces a portion of the air toward the underlying heat dissipator surface and a portion of the air outward toward the end sections of the housing. In any event, second hub 240 preferably includes openings 245 to permit air passage therethrough. Alternatively, second hub 240 may be fabricated as a pair of spaced-apart hoops that are spanned and joined by fins 210 on the exterior surface.

In FIG. 4, the direction of air flow is left-to-right, as shown by the parallel arrows on the left, and the rotational direction is as shown by the curved arrow ω. The inner axial blades 220 draw ambient air through fan housing vents 90 (see FIG. 1) into housing 20, and the radial outer blades 210 then move or circulate this air along plenums 180. This circulated air then evaporatively cools water-moistened surface 174 of plates 170. Surface 174 will have been wetted by water from sponge material 160 that, due to the absence of a moisture barrier at interface regions 162 (see FIG. 3) can move onto surface 174, promoted by wicking material 179. The air exits the plenum via openings 150' in the sponge material, and corresponding openings 150 in the upper and lower housing surfaces.

One may first treat the sponge material with an antibacterial anti-fungal solution. Such a solution can inhibit growth of undesired microorganisms within the cooler, promoting hygienic use of the cooler.

Understandably it is important that water be retained within sponge material 160 for efficient cooling to occur. Optionally, neck cooler 10 can be provided with a visual indicator 250 (see FIG. 1) to provide visual indication when material 160 is becoming dry. For example, material 250 may be a strip of thin water permeable material, cloth for example, impregnated with cobaltous chloride. This chemical will cause strip 250 to appear pink when wet, but blue when dry.

The present invention will provide effective cooling as long as metal plate surfaces 174 remain moist, and as long as fan 100 circulates air into and within housing 20. In practice, plate surfaces 174 can remain moist for 3 hours or more, and a typical AA battery 110 can power 100 for about 14 hours. Temperature reductions from ambient air temperature of up to about 20° F. are obtained at about 100° F. ambient and about 20% relative humidity. Even greater temperature reductions can be attained at increasing ambient temperature and/or decreasing relative humidity. These cooling reductions are attained without requiring a user to handhold a cooling device, and without exposing the user to water dripping onto the neck or clothing. While being thus cooled, the user can freely participate in all manner of indoor or outdoor activities including without limitation walking, jogging, bicycle riding, exercising, working, and motor vehicle operating.

While the present invention has been described with respect to a cooling device for a human, e.g., for use on the neck, forehead, or other body part, it will be understood that other animals may also benefit from the device. For example, a suitably sized device might be worn by pets. A guide dog for a blind person might especially benefit from a neck evaporator device on a hot day when excessive heat might otherwise impair the dog's ability to protect its owner.

It will also be appreciated that while the preferred embodiment has been described with respect to a self-retaining device, e.g., a "C"-shaped device that supports itself, the present invention could be fabricated as a flat device that is strapped or otherwise supported against a surface to be cooled. For example, a flat-shaped device according to the present invention could be strapped to a user's chest, back or other body region to promote cooling for comfort or perhaps for medical purposes.

Figure 5A:
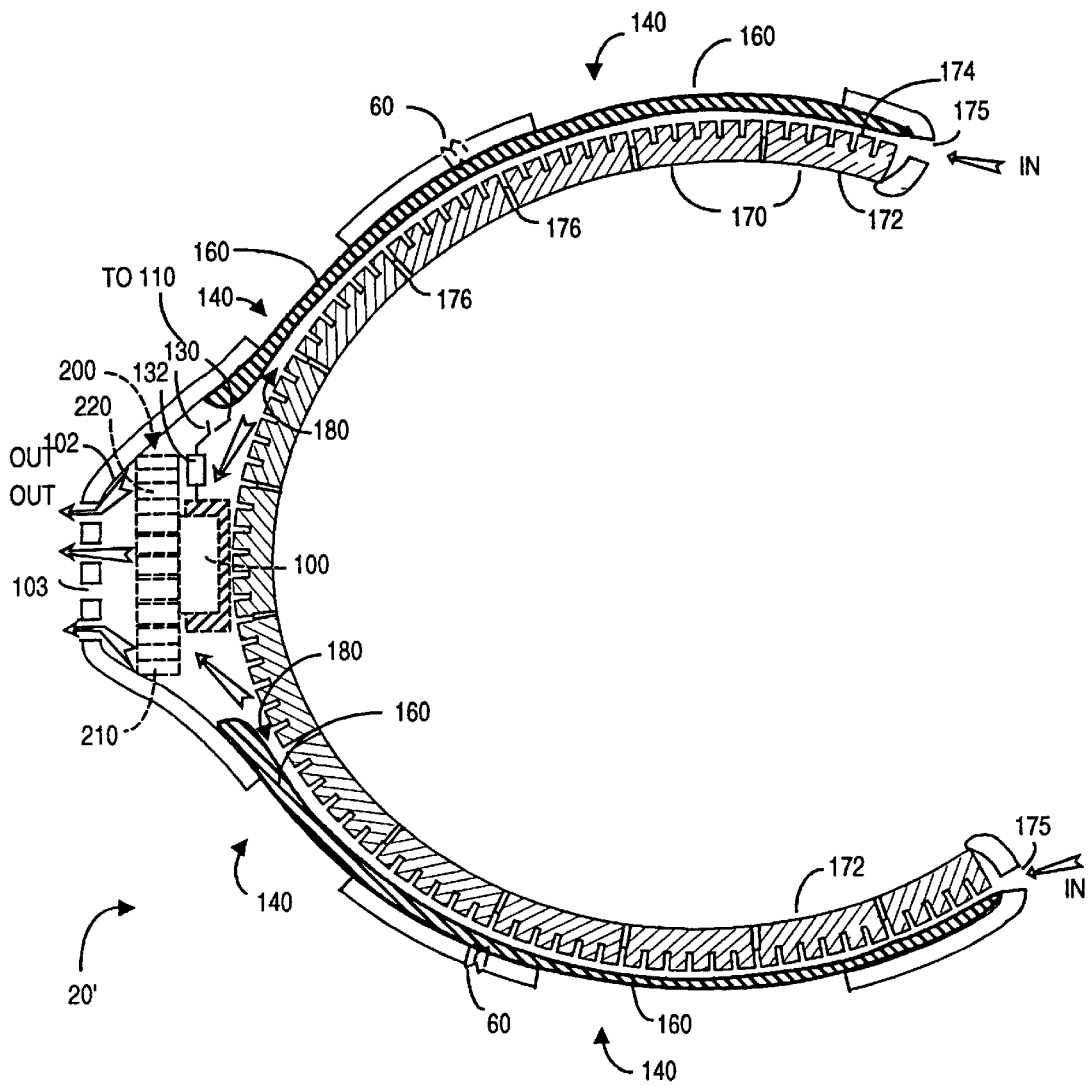
FIG. 5A is a perspective view of an alternative embodiment in which air flow is opposite from that in the embodiments of FIGS. 104, according to the present invention.

Turning now to FIG. 5A, a new embodiment is shown in which air flow is opposite from that associated with the embodiments of FIGS. 1–4. In FIG. 5A, one or more intake ports 175 are formed in a forward-facing region of device 20'. By forward-facing, it is meant that when device 20' is worn by a user, ports 175 will face generally forward. Note in FIG. 5A that motor 100 and fan assembly 200 are shown in phantom and reversed relative to the configuration of FIG. 4. Thus, motor 100 may be mounted closer to the front-facing region of device 20, with fan blade assembly 200 closer to the rear-facing region of device 20 if desired. In the configuration of FIG. 5A, air flow (denoted "IN") enters device 20' through intake ports 175, flows through plenums 180 and exits (denoted "OUT") via exit ports 103 (as well as through any other exit ports present). If air flow is active, then motor 100 and fan assembly 200 will be present, and will be configured to draw air into and through device 20', as shown by the hollow arrows.

On the other hand, the configuration of FIG. 5A can omit motor 100 and fan assembly 200. In the resultant configuration air passively enters ports 175, passively moves through device 20' (e.g., via plenums 180) and passively exits via ports 103 (and any other exit ports present). This passive movement results from relative motion of device 20' in ambient air. Thus, if device 20' is worn by a jogger, a bicyclist, etc., as the use moves forward, there will exist relative motion of ambient air relative to device 20', almost in ram-jet function. Although passive operation may be less effective than active operation where a motor and fan assembly is used, the resultant device will be lighter in weight, can be manufactured somewhat more compactly, and will be less expensive to produce.

FIG. 5A also depicts the optional inclusion of a motor speed control device 132, preferably electrically coupled between the windings of motor 100, switch 130 and power supply 110. Control device 132 may be used with any of the embodiments described herein, and preferably includes a two-pole (or more) thermostat. In practice, the present invention can actually function too well, that is, over-cool a user. Rather than require the user to manually activate switch 130 or even remove the invention, a thermostat or thermistor 132 can automatically help regulate the present invention.

Unit 132 senses temperature adjacent heat dissipator 170, and when this temperature falls below a predetermined threshold (perhaps in a range of about 60° F. to 70° F.) thermostat or other device 132 can open-circuit electrically. When device 132, which may be a simple bi-metal unit, open-circuits, operating power to motor 110 will be interrupted, which will stop the active (e.g., fan-moved) movement of air within the device plenum(s). When the monitored temperature at the heat dissipating member rises above the predetermined threshold, unit 132 will close, permitting motor 110 to become active, thus cooling the user. If desired, unit 132 could also provide a time-interrupt function such that once unit 132 opens, it will remain open for at least a given amount of time, e.g., perhaps 10 minutes. If desired, a usere-variable thermostat control can be provided, whereupon the threshold temperature may be user-selected.

If desired, unit 132 could include a thermostat and associated circuitry to regulate duty cycle of operating potential to motor 100. Thus, under normal operating conditions duty cycle may be close to 100%, as an "almost too cold" temperature is sensed, unit 132 can decrease duty cycle of voltage provided by battery 110 to cause fan assembly 200 to rotate more slowly. As temperature sensed at heat dissipator 170 begins to rise, unit 132 will cause motor rotational speed to increase, to maintain an acceptably cool, but not too cold, temperature where the heat dissipator member contacts the user's body.

Figure 5B:
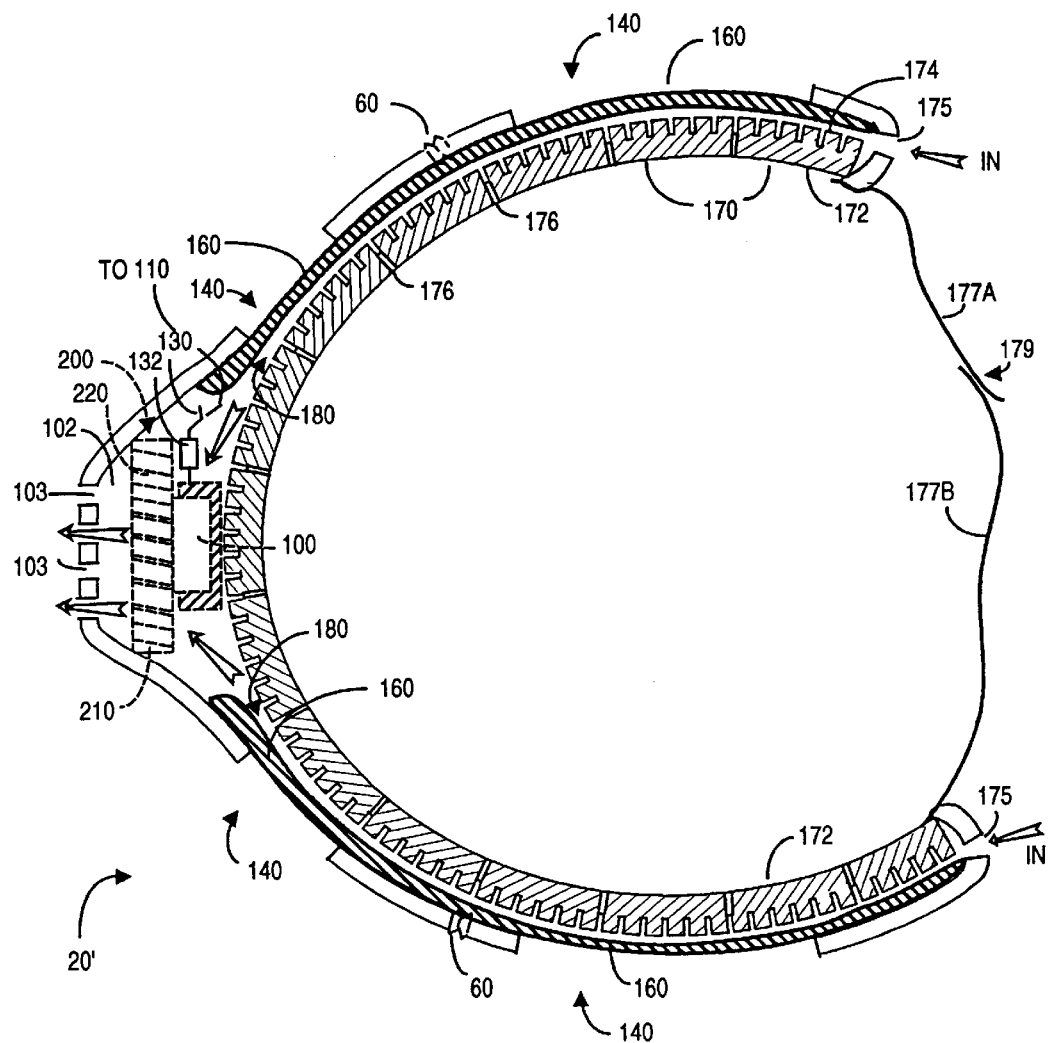
FIG. 5B is a perspective view similar to FIG. 5A, but in which an axial fan blade assembly is used, according to the present invention.

FIG. 5B depicts an embodiment similar to FIG. 5A, except that an axial fan blade assembly is used rather than a radial fan blade assembly, as shown in FIG. 5A. In general, a radial fan blade assembly (e.g., FIGS. 2 and 5A), in which the exhausted air comes from the side of the assembly, seems to be more efficient than an axial blade configuration in moving air under pressure for a given amount of electrical power. In FIG. 5A for ease of illustration exhaust vents are shown at the rear portion of the device. Understandably, efficiency may be promoted by disposing exhaust vents even closer to the fan assembly exhaust stream on the sides of the device.

In any of the embodiments of the present invention described herein, it is understood that a variety of fan blade assemblies may be used. FIG. 5B also depicts optional retaining belt portions 177A, 177B that engage each other at belt regions 179 to help secure the present invention to a user's body.

It will be appreciated from all of the foregoing that the present invention absorbs heat from the user's body via heat dissipating member 170, and provides liquid to the device-facing surface 174 of that member. An evaporation process from surface 174 occurs, which process is encouraged by the air flow (active or passive) through plenum(s) 180. The air flow takes on the moisture, which helps pull heat from dissipating member 170, which cools the user's body portion in contact with body-facing surface 172 of element 170.

Figure 6A:
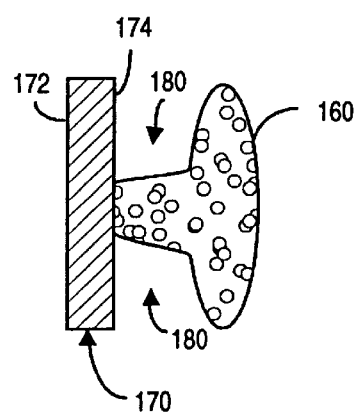
FIG. 6A is a cutaway view depicting multiple plenums in an alternative embodiment of the present invention.

The same process occurs in the embodiment of FIG. 6A, wherein liquid retainable material 160 contacts heat dissipating member 170 at at least one location rather than at at least two locations, as in the embodiment of FIG. 3. Indeed, in FIG. 6A, contact is made along the device-facing surface 174 rather than at the edges. As a result, two plenums 180 are formed. Material 160 may be the same sponge-like material as described earlier herein, although other materials may instead be used. In the embodiment of FIG. 6A (as in any of the other embodiments), heat dissipator element 170 may be a single continuous band of material rather than a series of linked shorter length material pieces. Of course, element 170 may be a series of linked shorter length material pieces. Preferably the regions of surface 174 subjected to moisture from material 160 will have been enlarged in area, using any of the methods or materials (or equivalents thereof) described herein. As practiced herein, the area of enlargement may be macroscopic or larger, or microscopic in magnitude. It will be appreciated that a device housing is not depicted in FIG. 6A.

Figure 6B:
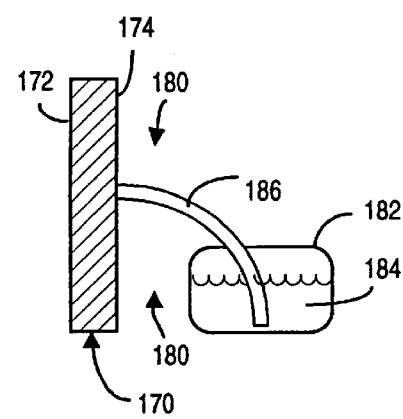
FIG. 6B is a cutaway view depicting use of reservoir and wick combinations in an alternative embodiment of the present invention.

In the embodiment of FIG. 6B, one or more reservoirs 182 contains a liquid 184 that is communicated through one or more wicks 186 to surface 174 of heat dissipating element 170. Wick 186 is made from a material that will conduct the liquid, cotton for example, although numerous other materials may instead be used. In practice, liquid 184 will be water but any high volatility, rapidly-evaporating liquid may be used. Alcohol, for example, would work better than water as liquid 184, but the exhaust fumes would likely intoxicate a wearer of the present invention. Where multiple reservoirs 182 are employed, they may be disposed at various locations along the length of heat dissipator element 170. Preferably there will be fluid communication between the reservoirs such that a single liquid intake port can be used to fill more than one reservoir with additional liquid 184.

Figure 6C:
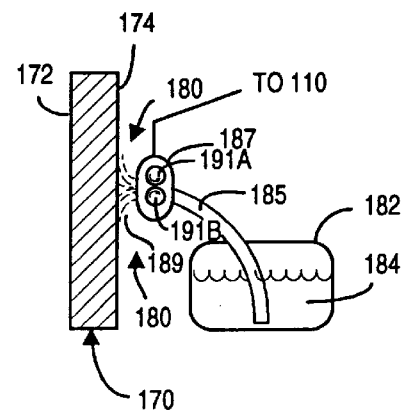
FIG. 6C is a cutaway view depicting use of pumps in an alternative embodiment of the present invention.

The embodiment of FIG. 6C augments what was shown in FIG. 6B by replacing wick 186 with a hollow tube 185 through which liquid 184 is drawn by a pump 187, energized by battery 110. Pump 187 preferably comprises two rotatable cogged gears 191A, 191B that are exposed to liquid 184 and create a mist-like spray 189. Essentially the liquid travels on the outer surface of the gears, and is expelled on an outlet side of the pump. Pump 187 directs the spray, e.g., through nozzles or the like, toward surface 174 of heat dissipator element 170. This carburetor-like spray could result in reduction or elimination of sponge-like material 160. However efficiency could suffer as the spray would moisten the preferably dry air within plenum(s) 180 that is desired to evaporatively remove heat from the heat dissipating member 170 and ultimately out of the present invention.

In the embodiments of FIGS. 6B and 6C, the absence (or at least curtailed size) of foam-like material 160 provides more volume within the device housing to store liquid 184. This in turn can allow the present invention to operate longer before replenishing the liquid supply. It will be appreciated that FIGS. 6B and 6C do not depict a housing for the device for ease of illustration It is understood that in any embodiment, device-facing surface 174 of the heat dissipating member preferably will be enlarged in effective surface area. As noted, an enlarged effective surface area promotes better transfer of heat from heat dissipator 170. Area enlargement may be accomplished using any of the techniques or methods described herein, or equivalents thereof.

Figure 6D:
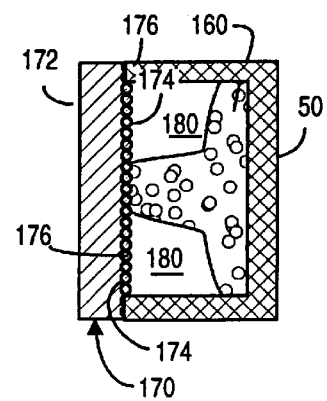
FIG. 6D is a cutaway view depicting use of wickable bead-like structures to enhance the device-facing area of the heat dissipating member, according to the present invention.

FIG. 6D shows an embodiment in which surface 174 of the heat dissipator includes bead-like particles 176 that collectively increase the effective area of surface 174. Particles 174 preferably are small in individual area and have a liquid wickable surface. Without limitation, particles 174 may be silicon carbide beads or powdered silicon carbide. Other materials may instead be used, the desired qualities being a liquid wickable characteristic, small individual size giving rise collectively to greater effective combined surface area, and ability to adhere to surface 174 of heat exchange element 170.

As an alternative to physical bead-like particles 176, a similar effect can be obtained by micro-grooving surface 174 to form channels, e.g., by machining, by sand blasting, by chemical treatment including etching, among other techniques known to those skilled in the art.

A device housing 50 is depicted in FIG. 6D as attaching to peripheral regions of surface 174 of the heat dissipator element 170. Such housing attachment is in contrast to the embodiments of FIGS. 1–3 and 5A and 5B in which the housing surrounded and retained peripheral regions of the user-facing surface 172 of the heat dissipator member.

Although for ease of illustration housing 50 is drawn as being somewhat semi-rectangular in cross-section, in practice housing 50 will likely have a more streamlined cross-section, e.g., a section of an ellipsoid. Further, it will be appreciated that the material comprising housing 50 preferably is lightweight and may itself be flexible, especially if housing 50 is a single flexible member rather than an assemblage of articulatable or hinged-together members. In some embodiments, housing 50 may not encompass a sufficient angular arc to be self-attaching to the user's body or may lack rigidity to be self-attaching. In such embodiments, one may attach a small length of belt or the like to one or both distal ends 70 of the device housing. Such a belt is shown in FIG. 5B in which distal ends 175 of the device housing are secured to belt portions 177A, 177B. The free end(s) of the belt portion(s) attach to one another at portion 179 using a length-adjustable attachment mechanism, e.g., via Velcro™-type material mating surfaces, a belt locking mechanism (not shown) or the like. Of course a single longer piece of belt could be used (e.g., portion 177A), the free end of this belt adjustably attaching to the other distal end of the device housing using any of a variety of attachment mechanisms. Of course, if desired, the present invention could be manufactured to encompass substantially a 360° circumference about the user's neck or other body portion. In such instance, a latch-type mechanism could attach distal ends 70 of the device to each other.

Figure 6E:
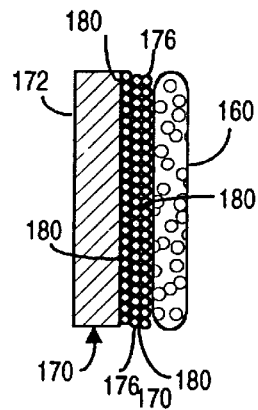
FIG. 6E is a cutaway view depicting use of wickable bead-like structures to enhance the device-facing area of the heat dissipating member, according to the present invention.

In the embodiment of FIG. 6E (which does not depict the housing for ease of illustration), device-facing surface 174 of the heat dissipating member now includes a thicker region of beads 176 (or the like), and liquid retaining foam or other material 160 now contacts more of surface 174. Note that a plurality of micro-plenums or channels 180 is defined in the thicker region of beads 176. If desired, when attaching bead-like wickable elements 176 to surface 174, rod or channel members may be left in place to define through-plenums, and removed (or lost due to melting) preceding or following the attachment process. These multiple plenums and/or micro-plenums permit fabricating the present invention with a shallower housing configuration, front-to-back. Stated differently, a cross-section of the embodiment of FIG. 6E can be shallower than a cross-section of the embodiment of FIG. 6A or of FIG. 1 or 2, etc.

Figure 6F:
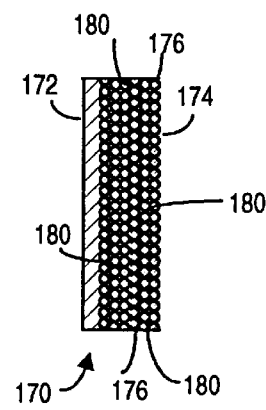
FIG. 6F is a cutaway view depicting use of porous device-facing area of the heat resulting from micro-grooving, micro-channelling, or use of wickable members, according to the present invention.

In the embodiment of FIG. 6F, the device-facing surface 174 of the heat dissipating element has been made extremely porous due to the presence of micro-grooving or micro-channelling, resulting from wickable members 176. Indeed, so many micro-plenums 180 are formed that, but for its stiffness, device-facing surface 174 now acts somewhat sponge-like, and indeed material 160 may be omitted. In this embodiment, as in the embodiments of FIGS. 6A and 6E, liquid may be introduced onto surface 174 using wicking (as shown in FIG. 6B), or actively mist-spraying (as shown in FIG. 6C) or by saturating surface 174 with liquid (as in the embodiments of FIGS. 1–3), as though surface 174 were sponge-like material 160.

Figure 6G:
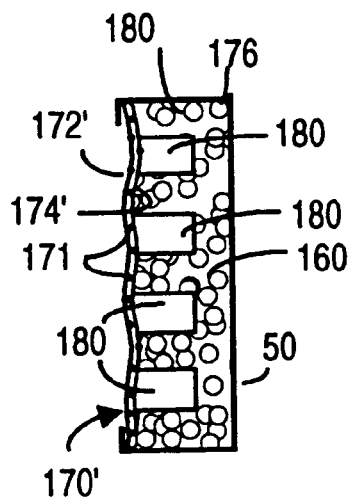
FIG. 6G depicts use of a cloth heat dissipating member in an alternative embodiment of the present invention.

The embodiment of FIG. 6G recognizes that a sufficiently micro-grooved or porous heat dissipating element 170 can, if sufficient micro-plenums are formed, take on the characteristics of a fabric material, cotton or felt for example. Thus, in FIG. 6G, heat dissipating element 170' is indeed a piece of fabric. For a neck-sized cooling device, fabric 170' might be perhaps 10" (25.4 cm) in length and perhaps an inch (1 cm) wide, although other dimensions could of course be used.

In the embodiment of FIG. 6G, sponge-like material 160 is formed with fabric-facing extensions to define a plurality of plenums 180 between the extensions. This construction permits forming plenums with substantial openings, while simultaneously providing support against the device-facing surface 174' of fabric material 170'. Of course more or fewer extensions and plenums could be formed, and different plenums may have different dimensions. In the embodiment of FIG. 6G, unless housing 50 is sufficiently rigid and user-body conforming in shape, belt(s) 177A/B such as shown in FIG. 5B will be used to secure the device to the user's body.

It will be appreciated that a fabric heat sinking element will be light weight, less expensive to produce, and more conforming than a metal or other more rigid material. If desired, fabric material 170' may include beads 171, typically a polymer or other material that can absorb moisture. In the embodiment shown in FIG. 6G, housing 50 urges fabric material 170' against sponge-like material 160. If desired, a wire or plastic grid or mesh could be disposed behind fabric 170' to provide additional rigidity, while still allowing the present invention to flexibly conform to a desired portion of the user's body.

Figure 6H:
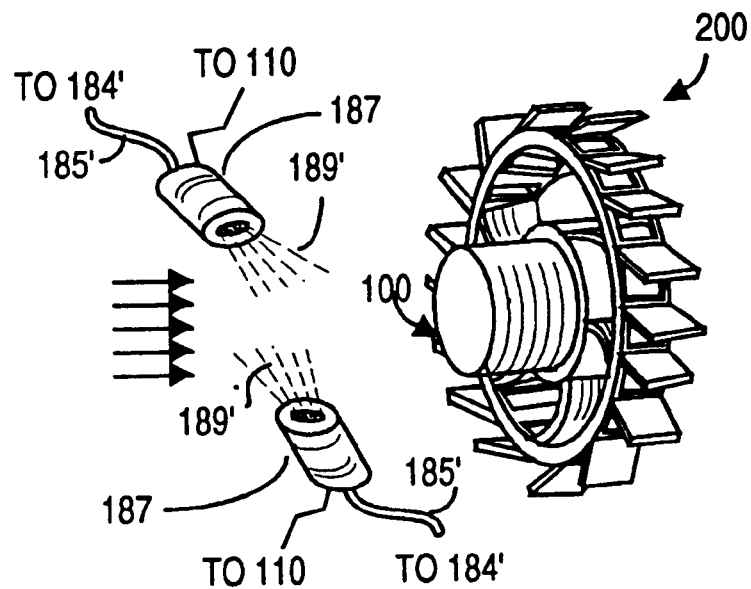
FIG. 6H depicts use of pumps and reservoirs and a fan unit to move water mist through the present invention.

In the embodiment of FIG. 6H, one or more pumps 187 directs a spray 189' of water drawn from reservoir(s) 184' via tubes 185'. The pump(s), reservoir(s) and tube(s) may be as described with respect to FIG. 6C. Augmenting the intake air with a water mist may be used with any or all of the embodiments described herein. It will be appreciated that other fan blade assembly configurations may of course be used.

It will be appreciated that essentially any of the disclosed embodiments may be fabricated as modules, to better accommodate fitting to user's necks, foreheads, etc., having different circumferences. Although more efficient cooling can be promoted by surrounding a greater area of the user's body portion with the present invention, modular portions of the invention could be spaced-apart from each other along a common belt mechanism. Such belt mechanism would secure the modules, which might measure perhaps one square inch (6.2 cm$^2$) or more each in surface area, along a circumference encompassing the user's neck or other body portion. Preferably a single battery power supply would drive fan(s) in each module.

If desired, other means for indicating moisture content of the liquid-retaining material and/or any reservoirs may be provided. As noted, passive visual means may be chemically implemented. If desired, visual means (e.g., a blinking light emitting diode), audible means (e.g., a beeping sound) could also or instead be provided. If desired, an entertainment device could readily be incorporated into the present invention, for example a small AM-FM radio. The physical appearance of the present invention may also be changed from what has been described or suggested. For example, to minimize moisture loss due to dripping, it may be desirable to locate all vents or ports on an upper region of the device housing.

Modifications and variations may be made to the disclosed embodiments without departing from the subject and spirit of the invention as defined by the following claims.

What is claimed is:

1. A device for cooling a body portion of a user, comprising:

a heat dissipating member biasable toward said body portion;

a liquid-retainable material disposed to contact at least one region of said heat dissipating member and defining at least one plenum between a region of said heat dissipating member and a region of said liquid-retainable member; and means for moving air along said plenum and out of said device.

2. The device of claim 1, further including a housing having at least one characteristic selected from a group consisting of (a) said housing is articulatable to conform to at least a part of said body portion, (b) said housing urges said heat dissipating member toward said body portion, (c) said housing is attached to said heat dissipating member, (d) said housing encloses said liquid-retainable material, (e) a surface of said housing defines at least one air intake port, (f) a surface of said housing defines at least one air exhaust port, (g) a surface of said housing defines at least one liquid intake port, and (h) said housing encompasses at least 180° of a circumference of said body portion.

3. The device of claim 1, wherein said heat dissipating member has at least one characteristic selected from a group consisting of (a) a plenum-facing surface of said member has a surface area greater than a user-facing surface of said member, (b) a plenum-facing surface of said member has a liquid-wickable surface, (c) a plenum-facing surface of said member includes at least one layer of beads comprising a liquid-wickable material, (d) a plenum-facing surface of said member includes micro-grooves, (e) a plenum-facing surface of said member defines at least one micro-plenum, (f) a plenum-facing surface of said member defines sand-blasted crevices, (g) a plenum-facing surface of said member defines acid-etched crevices, (h) said member comprises a plurality of linked-together elements, and (i) said member is a single length of metal.

4. The device of claim 1, wherein said heat dissipating member has at least one characteristic selected from a group consisting of (a) said member comprises a fabric, (b) said member comprises a fabric containing liquid-absorbing material, (c) said member comprises a fabric containing liquid-absorbing beads, and (d) said member comprises a fabric containing polymer material.

5. The device of claim 1, wherein said liquid-retainable material has at least one characteristic selected from a group consisting of (a) said material is a foam-like porous liquid absorbing material, (b) said material includes cellulose sponge, (c) said material includes a moisture barrier surface at regions other than an interface with said heat dissipating member, (d) said material in cross-section defines a "C"-shape, (e) said material in cross-section defines an "E"-shape, (f) said material in cross-section includes a portion defining an "E"-shape, (g) said material in cross-section defines a sideways "T"-shape, (h) said material in cross-section defines a rectangle, and (i) in use said material is saturated with water.

6. The device of claim 1, further including:
    a reservoir fillable with liquid retainable by said liquid retainable material; and
    means, coupled to said reservoir, for delivering said liquid to a plenum-facing surface of said heat dissipating member.

7. The device of claim 6, wherein said means for delivering includes at least one mechanism selected from a group consisting of (a) a liquid absorbing member having a first member portion in fluid communication with said reservoir and having a second member portion in communication with said plenum-facing surface, (b) a liquid absorbing member having a first member portion in fluid communication with said reservoir and having a second member portion in communication with said plenum-facing surface wherein said liquid absorbing member includes a moisture barrier surface at regions other than an interface with said reservoir and said plenum-facing surface, and (c) a pump and a liquid conduit having a first conduit end in fluid communication with said reservoir and a second conduit end in fluid communication with an input of said pump such that said pump outputs a spray of said liquid toward said plenum-facing surface.

8. The device of claim 1, wherein said means for moving air includes at least one mechanism selected from a group consisting of (a) a motorized fan driving a fan blade assembly, (b) a motorized fan driving a fan blade assembly with a rotation that a function of temperature at said heat dissipating member, (c) a motorized fan driving a fan blade assembly and means for spraying liquid into an output stream of air created by said fan blade assembly, (d) a motorized fan driving a fan blade assembly having inner axially disposed blades and concentric outer radially disposed blades, (e) a motorized fan driving a fan blade assembly having inner axially disposed blades and outer axially disposed blades, (f) a motorized fan driving a fan blade assembly having inner radially disposed blades and outer radially disposed blades, and (g) at least one air intake port defined in a forward-facing direction of said device such that air moves passively into said plenum via said port.

9. The device of claim 1, further including a housing sized to fit conformably against at least a part of said body portion;
    said heat dissipating member being attached to said housing such that at least a portion of a plenum-facing surface of said member faces said housing, said plenum-facing surface having greater surface area than a body portion-facing surface of said member; and
    said liquid-retainable material being disposed within said housing so as to contact at least a chosen one of an upper region and a lower region of said member while being spaced-apart from said plenum-facing surface thereof to define said plenum.

10. The device of claim 1, further including at least one of (a) means for indicating moisture content of said liquid retaining material, (b) visual means for indicating moisture content of said liquid retaining material, and (c) a user-operable thermostat to control operation of said means for moving air as a function of temperature sensed at said heat dissipating member.

11. The device of claim 1, further including a housing sized to fit conformally against at least a port of said body portion, wherein said heat dissipating member is attached to said housing and said liquid-retainable material is disposed within said housing, said housing including at least:
    a central housing portion;
    a first housing portion;
    a second housing portion;
    wherein said central housing portion is articulatably linked between said first housing portion and said second housing portion.

12. The device of claim 11, wherein said heat dissipating member has at least one characteristic selected from a group consisting of (a) said member includes one metal plate for said first housing portion and one metal plate for said second housing portion, (b) said member includes at least two metal plates for at least one of said first housing portion and said second housing portion, (c) said member includes a plurality of metal plates adjacent ones of which are biasedly joined together such that said metal plates are conformably urged toward said body portion, (d) a plenum-facing surface of said member has a surface area greater than a user-facing surface of said member, (e) a plenum-facing surface of said member has a liquid-wickable surface, (f) a plenum-facing surface of said member includes at least one layer of beads comprising a liquid-wickable material, (g) a plenum-facing surface of said member includes micro-grooves, (h) a plenum-facing surface of said member defines at least one micro-plenum, (i) a plenum-facing surface of said member defines sand-blasted crevices, and (j) a plenum-facing surface of said member defines acid-etched crevices.

13. The device of claim 11, wherein said liquid-retainable material has at least one characteristic selected from a group consisting of (a) said material is a foam-like porous liquid absorbing material, (b) said material includes cellulose sponge, (c) said material includes a moisture barrier surface at regions other than an interface with said heat dissipating member, (d) said material is disposed within said housing so as to contact at least one region of a plenum-facing surface of said member and to define said plenum, and (e) said material is disposed within said housing so as to contact a chosen one of an upper region and a lower region of said heat dissipating member while being spaced-apart from a plenum-facing surface thereof so as to define at least one said plenum.

14. The device of claim 11, wherein said means for moving air includes at least one mechanism selected from a group consisting of (a) a motorized fan driving a fan blade assembly, (b) a motorized fan driving a fan blade assembly with a rotation that a function of temperature at said heat dissipating member, (c) a motorized fan driving a fan blade assembly having inner axially disposed blades and concentric outer radially disposed blades, (d) a motorized fan driving a fan blade assembly having inner axially disposed blades and outer axially disposed blades, (e) a motorized fan driving a fan blade assembly having inner radially disposed blades and outer radially disposed blades, and (f) at least one air intake port defined in a forward-facing direction of said device such that air moves passively into said plenum via said port.

15. A self-contained device for cooling a body portion of a user, comprising:

housing conformable around at least a portion of a circumference of said body portion;

a heat dissipating member, retained by said housing, biasable toward said body portion, a plenum-facing surface of said member having an affinity for liquid;

a liquid-retainable material disposed within said housing to contact at least one region of said heat dissipating member and to define at least one said plenum between a region of said heat dissipating member and a region of said liquid-retainable member; and a battery operable fan that moves air along said plenum and out of said housing.

16. The device of claim 15, wherein said plenum-facing surface of said member has at least one characteristic selected from a group consisting of (a) said plenum-facing surface of said member has a surface area greater than a user-facing surface of said member, (b) said plenum-facing surface of said member has a liquid-wickable surface, (c) said plenum-facing surface of said member includes at least one layer of beads comprising a liquid-wickable material, (d) said plenum-facing surface of said member includes micro-grooves, (e) said plenum-facing surface of said member defines at least one micro-plenum, (f) said plenum-facing surface of said member defines sand-blasted crevices, (g) said plenum-facing surface of said member defines acid-etched crevices, (h) said member comprises a plurality of linked-together elements, (i) said member comprises a plurality of metal elements, and (j) said member is a single length of metal.

17. The device of claim 16, wherein said liquid-retainable material has at least one characteristic selected from a group consisting of (a) said material is a foam-like porous liquid absorbing material, (b) said material includes cellulose sponge, (c) said material includes a moisture barrier surface at regions other than an interface with said heat dissipating member, (d) said material in cross-section defines a "C"-shape, (e) said material in cross-section defines an "E"-shape, (f) said material in cross-section includes a portion defining an "E"-shape, (g) said material in cross-section defines a sideways "T"-shape, (h) said material in cross-section defines a rectangle, and (i) in use said material is saturated with water.

18. A method for cooling a portion of a user's body with a self-contained device, the method comprising the following steps:

(a) biasedly urging a user-facing surface of a heat dissipating member against said portion;

(b) disposing a liquid-retaining material saturated with liquid such that said material contacts at least one region of said member while being spaced-apart therefrom to define at least one plenum, wherein liquid from said material may moisten said at least one region of said heat dissipating member; and (c) moving air through said plenum and out of said device to promote evaporation of said liquid from said at least one region of said heat dissipating member;

wherein evaporation of said liquid from said member lowers temperature of said member and cools said portion of said user.

19. The method of claim 18, wherein step (a) includes providing a heat dissipating member whose plenum-facing surface has at least one characteristic selected from a group consisting of (a) said surface has a surface area greater than said user-facing surface of said member, (b) said surface is liquid-wickable, (c) said surface includes at least one layer of beads comprising a liquid-wickable material, (d) said surface includes micro-grooves, (e) said surface defines at least one micro-plenum, and (f) said surface defines sand-blasted crevices, (g) said surface defines acid-etched crevices.

20. The method of claim 18, wherein step (b) includes providing a liquid-retainable material having at least one characteristic selected from a group consisting of (a) said material is a foam-like porous liquid absorbing material, (b) said material includes cellulose sponge, (c) said material includes a moisture barrier surface at regions other than an interface with said heat dissipating member, (d) said material is disposed within said housing and saturated with water, (e) said material in cross-section defines a "C"-shape, (f) said material in cross-section defines an "E"-shape, (g) said material in cross-section includes a portion defining an "E"-shape, (h) said material in cross-section defines a sideways "T"-shape, and (i) said material in cross-section defines a rectangle.

* * * * *